United States Patent [19]
Weber-Unger et al.

[11] Patent Number: 6,113,634
[45] Date of Patent: Sep. 5, 2000

[54] BREAST PROSTHESIS AND METHOD FOR MAKING THE SAME

[75] Inventors: Georg Weber-Unger, Kufstein, Austria; Stephan Volk, Miesbach, Germany

[73] Assignee: F + E Gesellschaft für Bekleidungsinnovation mbH & Co. KG, Brannenburg, Germany

[21] Appl. No.: 08/844,813

[22] Filed: Apr. 22, 1997

[30] Foreign Application Priority Data

Apr. 23, 1996 [DE] Germany .......................... 196 16 190
Jan. 15, 1997 [DE] Germany ........................ 297 00 642 U
Mar. 13, 1997 [DE] Germany ........................ 297 04 605 U

[51] Int. Cl.$^7$ ..................................................... A61F 2/52
[52] U.S. Cl. ..................................................... 623/7; 623/8
[58] Field of Search ........................... 623/7, 8; 450/38, 450/39, 55, 54

[56] References Cited

U.S. PATENT DOCUMENTS

| | | |
|---|---|---|
| 2,516,129 | 7/1950 | Leo et al. .................................. 450/55 |
| 3,706,104 | 12/1972 | Dehlin et al. ............................... 623/7 |
| 3,852,833 | 12/1974 | Koneke et al. ............................... 623/7 |
| 4,125,177 | 11/1978 | Lee . |
| 4,828,559 | 5/1989 | Greenberg .................................... 623/7 |
| 5,098,330 | 3/1992 | Greenberg ................................. 450/55 |
| 5,603,791 | 2/1997 | Weber-Unger et al. ................. 156/145 |
| 5,902,335 | 5/1999 | Snyder, Jr. .................................. 623/7 |

FOREIGN PATENT DOCUMENTS

DE 44 21 516  7/1995  Germany .
WO 94 16650  8/1994  WIPO .

*Primary Examiner*—David H. Willse
*Assistant Examiner*—Suzette J. Jackson
*Attorney, Agent, or Firm*—Henry M. Feiereisen

[57] ABSTRACT

The invention relates to a breast prosthesis for breast-amputated women with a flexible plastic body (1) comprising two plastic sheets (2, 3) connected to each other along their common edge (23) and a plastic mass (4) enclosed between the two plastic sheets (2, 3), wherein the plastic body (1) has a front side (21) formed to resemble the contour of the natural breast and a back side (31) capable of facing the torso of the person, and an elastically deformeable thin part (6) secured with its edge (611) to the back side (31) of the plastic body (1). In order to improve the wear comfort of the breast prosthesis, the thin part (6) is secured to the plastic body (1) inside the common edge (23) of the connected plastic sheets (2, 3).

32 Claims, 8 Drawing Sheets

BREAST PROSTHESIS AND METHOD FOR MAKING THE SAME

TECHNICAL FIELD

The invention relates to a breast prosthesis with a flexible plastic body comprising two plastic sheets connected to each other along their common edge and a plastic mass enclosed between the two plastic sheets, wherein the plastic body has a front side formed to resemble the shape of the natural breast and a back side capable of facing the torso of the wearer, and an elastically deformeable thin part secured with its edge to the back side of the plastic body. The invention also relates to a method for making the breast prosthesis. Breast prosthesis of this type are worn in bras, bikini tops, swimsuits and the like.

PRIOR ART

A breast prosthesis of this type is known from DE 44 21 516 C1. The state of the art provides a breast prosthesis which is very comfortable to wear and has a natural appearance. Since breast prosthesis are often worn for a long time and in addition simulate a part of the body which is very important for the self esteem of the woman, even slight improvements in the wear comfort and in the simulation of the natural appearance, respectively, represent a significant progress.

OBJECT OF THE INVENTION

It is the object of the invention to design the breast prosthesis in such a way that the wear comfort and the simulation of the natural appearance, respectively, are further improved, as well as to provide a method for the manufacture thereof.

The object is solved with the features of the claim 1 and 31, respectively. Advantageous embodiments are provided in the dependent claims.

Since the prosthesis in the edge regions preferably only includes the plastic sheets enclosing the plastic mass, an almost continuous or natural transition between the prosthesis and the skin of the wearer can be achieved. This advantage of the embodiment of the invention is particularly evident when fabric material is used for the thin part, since the thickness of the fabric material requires a stepped transition.

Some wearers prefer to wear the breast prosthesis directly on their skin. With the embodiment of the invention, the risk that the prosthesis slips is reduced, which could otherwise make an unnatural and thus undesirable impression. Here, the edge portion of the prosthesis is not covered by the thin part which is made preferably of fabric material, and advantageously has a larger friction coefficient than the thin part when it makes contact with the skin of the wearer. This effect is enhanced by the natural moistness of the skin.

After partial amputations or after reconstruction of a new, but smaller breast after a full amputation, cup prosthesis are preferably used which only simulate the contour of a portion of the natural breast. In order to provide a transition between the remaining or reconstructed breast and the prosthesis which appears as natural and continuous as possible, the thickness of the plastic body of such cup prosthesis usually decreases towards the edge. As a result, the thickness and thus the stiffness of the flexible plastic body is reduced in comparison to a full prosthesis. According to the invention, the possibility for the edge of the plastic body to curl up as a result of the force created by the tension of the thin part is reduced, since the thin part is displaced towards the inside. The plastic body is therefore at most dented, but never curls. The deformation is further reduced by the increased wall thickness of the plastic body and the increased stiffness resulting therefrom. Preferably, the thin part is secured to the back side of the plastic body 1 to 4 cm inside the edge of the breast prosthesis. This distance can vary, preferably with the size of the breast to be simulated and with the point of attachment.

Preferably, an opening is provided in the thin part and/or between the thin part and the plastic body for inserting filler material between the thin part and the back side of the breast prosthesis. In this way, the prosthesis can be individually fitted to the upper body, i.e. to the remaining breast or to the breast to be reconstructed, respectively. In particular, changes can be accommodated. In addition, the wearer herself can adjust the position of the filler material by trial and error for providing a better wear comfort and fit of the prosthesis.

Preferably, the thin part is deep drawn in such a way that a tensionless fit with the concave form of the back side of the plastic body is provided, which has the advantage that the thin part also contacts without tension the breast tissue which is left or remains intact after a partial amputation, thereby providing enhanced wear comfort.

It is another advantage of the breast prosthesis of the invention that it can be used as a cup evening out a breast, both for a breast reduction and for a breast enlargement. Furthermore, the breast prosthesis can easily be adapted to the changing volume and weight of the breast during the course of a step-by-step reconstruction through a step-by-step reduction of the filler material.

On the breast prosthesis of the invention, the thin part is secured to the plastic body inside the common edge of the plastic sheets connected to each other. In this way, the thin part is located closer to the front part of the breast or, expressed differently, farther inward of the breast prosthesis. Furthermore, a material can advantageously be selected for the thin part which is molded not at all or only slightly during the deep drawing process, but which is elastic enough so that the thin part essentially regains the same surface area it had before the deep drawing process. This creates an area with only slight tension. In first approximation, the breast prosthesis of the invention can then be regarded as an elastic hollow body. If a force is applied to an elastic hollow body as to compress it in one direction, then the cross sectional area between the delimiting surfaces increases. This enlargement is, for example, greatest for a cylinder or a sphere at their respective centers. If the envelope of the hollow body is connected along the cross sectional area, then the connection means will also be distorted when the cross sectional area increases. The force necessary to accomplish this opposes the compressing force. In addition to the rigidity residing in the envelope, the body is reinforced by connecting means opposing the increase in cross section.

In a breast prosthesis of the invention of this type, the plastic body is at its attachment line reinforced by the thin part, in addition to having its own rigidity. With the same stiffness, the breast prosthesis can thus be constructed to have less weight, whereby the wear comfort is enhanced. In addition, the breast prosthesis can be manufactured less expensively. Depending on the requirement for and the size of the breast to be simulated, one, two or more thin parts can be connected to the plastic body. Through a suitable selection of the number and the placement of the thin parts, the breast prosthesis can be optimally fitted to resemble the features of the natural breast. Satisfactory results are achieved with a first thin part in the rearward third and a second thin part in the forward third of the breast prosthesis.

In order to increase the wear comfort for women who do not desire a direct contact between the plastic sheet of the breast prosthesis and their skin, the thin part closest to the torso of the wearer is preferably enlarged by a marginal section extending to the common edge of the plastic sheets, wherein the marginal section contains preferably microfibers.

Advantageously, the outer edge of the marginal section is joined to the plastic body using the same method which is used for connecting the two plastic sheets. This can be accomplished by welding or gluing. The fixed connection between the outer edge of the marginal section and the plastic body allows the outer edge exactly to be even with the edge of the plastic sheets. An overhanging edge which could protrude from the garment under which the breast prosthesis is worn, is thereby avoided.

The marginal section of the thin part is advantageously joined to the back side facing the torso of the wearer in form of a grid pattern. This can, for example, be done by a welding operation using a tool having a grid pattern. A secure and slip-free fit of the thin part and consequently of the breast prosthesis is thereby ensured. Also reduced is the danger that the breast prosthesis slides and thereby causes unnatural effects.

The breast prosthesis contacts the torso of the wearer only along the marginal region. The sensitive skin and scar tissue are to a large extent ventilated, thereby accelerating for a freshly amputated wearer the scarring process and promoting an environment which does not irritate the skin. The continuous movement on the body causes a suction and pump effect which ensures an exchange of air between the skin and the prosthesis.

Placement of the thin part inside the edge of the plastic body creates a cavity capable of receiving breast tissue which is left after a partial amputation, without causing a troublesome pressure contact between the thin part and the remaining breast tissue. If, however, more breast tissue can be saved during a partial amputation than the cavity is capable of receiving without creating a contact between the breast tissue and the thin part, then the remaining breast tissue presses less strongly against the thin part than is the case with a breast prosthesis where the thin part is secured to the edge of the plastic body.

Preferably, the thin part is made of a microfiber or a climatic fabric. Since sweat in the form of steam can penetrate such material, but is prevented from returning to the skin of the wearer when in condensed form, the skin remains comfortably dry even under considerable bodily exertion.

Instead of joining the thin part to the plastic body by welding, the thin part can also be glued to the plastic body. Gluing also provides a secure and durable connection between the parts. The material should be secured by gluing if the material selected for the thin part cannot be welded at all or only with great difficulty, for example, when the material is made entirely or in part of a natural fiber, such as cotton.

Welding the thin part to the plastic body does not necessarily mean that the thin part completely fuses together with the plastic body. In this specification, the term "welding" shall also describe an attachment method wherein the thin part only fuses with the adjacent plastic sheet of the plastic body at its respective surface.

A variety of different materials can be used for the thin part. The major criteria for selecting the material to be used for the thin part is that the material can be easily attached to and released from the plastic body, and must have a desired elasticity and stiffness, respectively, a high tear resistance, good ability to absorb and release moisture, a comfortable softness and must be easy to clean. If the thin part is to be welded to the plastic body, then the thin part is preferably made of polyamide or polyester fibers. The thin part can be made at least in the marginal region of cotton or of a mixture of polyamide and/or polyester fibers and cotton because these materials are known for not irritating the skin. If the thin part should be capable of transporting the moisture away from the skin surface, then the thin part is advantageously a woven or knitted fabric made of microfibers which is pervious to moisture in the form of steam, but prevents condensated moisture from permeating. Particularly suited are extremely fine fibrillated microfibers made of polyester and polyamide. Such microfiber fabrics are known in the art as "climate fabrics". The different sections can be made of different materials depending on the different requirements. For example, the front thin part in particular preferably comprises a plastic sheet made of, for example, polyurethane.

Preferably, in the breast prosthesis there is provided an opening for inserting filler material into the cavity located between the tensioned surface(s) and the back side facing the torso of the wearer. The opening is preferably reclosable, in particular using a Velcro closure. The opening can be provided in the weld seam between the thin part and the back side facing the torso of the wearer or in the thin part itself. The filler material is preferably a padding element, in particular a microfiber thread ball or an air-tight film ball or a foam element. The opening is advantageous in that the padding element can be removed and enlarged.

The opening for filling the breast prosthesis preferably includes an element for reinforcing the fabric edges. For this purpose, there is disposed between the fabric member and the fabric tape a plastic sheet which is welded or glued to the fabric member and the fabric tape. Thereby a laminate comprising the fabric member, the fabric tape and the plastic sheet is created at the marginal region of the fabric member, wherein the laminate reliably protects the edge of the fabric member and also the edge of the fabric tape from fraying, can be manufactured economically, is not or is only marginally thicker than the fabric member and the fabric tape when both the fabric member and the fabric tape are superposed, and wherein the laminate does not change the appearance of the fabric member or the appearance of the fabric tape.

Preferably, the plastic sheet(s) is (are) polyurethane films which can be made very thin, extremely elastic and transparent and can be welded well to the fabric member and the fabric tape.

In addition, the fabric member and the fabric tape can be made of the same material, preferably of a fabric made of polyamide or polyester fibers, whereby the adhesion between the plastic sheet and the fabric member and the adhesion between the plastic sheet and the fabric tape is identical.

BRIEF DESCRIPTION OF THE DRAWINGS

Different embodiments of the invention are depicted in the drawings and are described in greater detail hereinafter. The thickness of the plastic sheets and the fabric member is exaggerated herein in comparison with the dimensions of the breast prosthesis.

It is shown in.

PREFERRED EMBODIMENTS OF THE INVENTION

Figure 1:
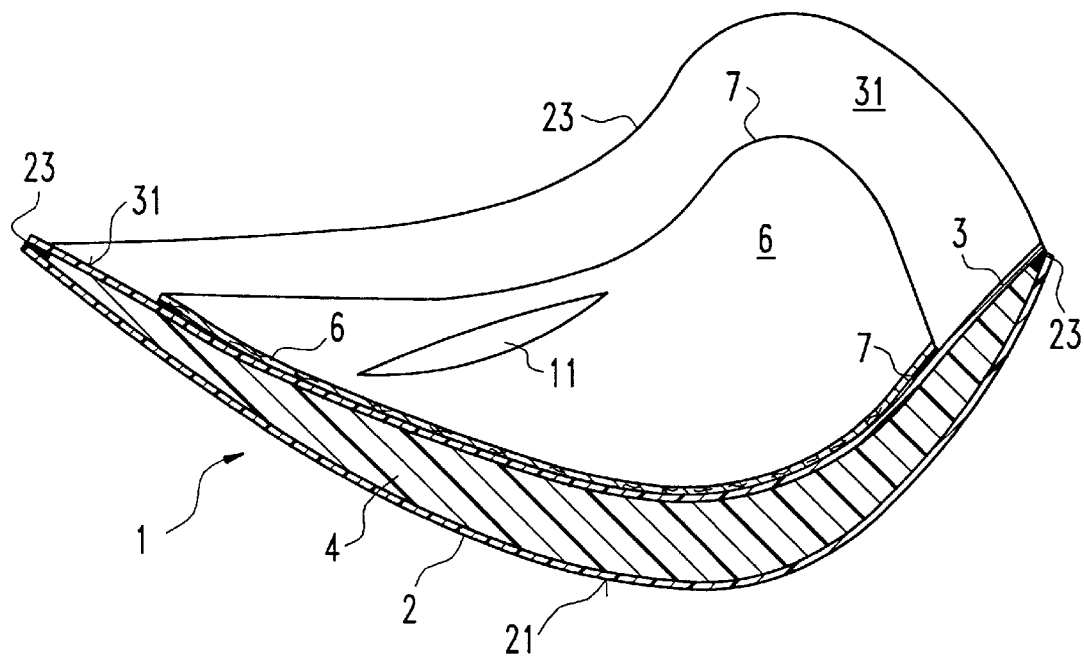
FIG. 1 a cross-sectional view of the breast prosthesis of the invention.

The breast prosthesis depicted in FIG. 1 represents a preferred embodiment of the invention. The breast prosthesis comprises a flexible, cup-shaped plastic body 1 made of two polyurethane films 2, 3 which are welded together along their common edge 23, and a two component cross-linked silicone rubber mass 4 which is enclosed cavitation-free between the polyurethane films. The side 21 of the polyurethane film 2 facing away from the silicone mass 4 has a convex shape corresponding to the shape of the natural breast. The side 21 of the polyurethane film 2 represents the front side of the plastic body 1 and thus the front side of the breast prosthesis. The side 31 of the polyurethane film 3 facing away from the silicone mass 4 has a concave shape, wherein the concave shape approximately matches the contour of the front side of the plastic body. This side 31 of the polyurethane film 3 represents the back side of the plastic body 1 facing the body of the wearer of the prosthesis. To the back side of the plastic body 1, there is fixedly connected an elastically deformeable fabric member (thin part) 6 through at least one weld or glue seam 7. The at least one weld or glue seam 7 extends inside the common edge 23 of the two plastic sheets 2, 3. The seam can be continuous or can include partial seams having in the longitudinal direction one or more separations therebetween which can be utilized, for example, as fill opening(s) for filler material.

The depicted embodiment represents a cup prosthesis for augmenting a remaining or reconstructed breast symmetrically to the intact breast. Since a person is usually not completely symmetrical, the reproduced breast can be reproduced somewhat larger or smaller, depending on the preference of the wearer.

The cup prosthesis tapers off towards the edge of the plastic body in order to preferably provide a continuous transition between the skin of the wearer and the prosthesis.

The back side 31 of the plastic body between the common edge 23 of the two plastic sheets 2, 3 and the fabric member 6 is preferably not covered by a fabric member. This increases the friction when the prosthesis is worn directly on the skin and thereby reduces the danger that the prosthesis slips which could result in a disfigurement of the wearer.

Figure 2:
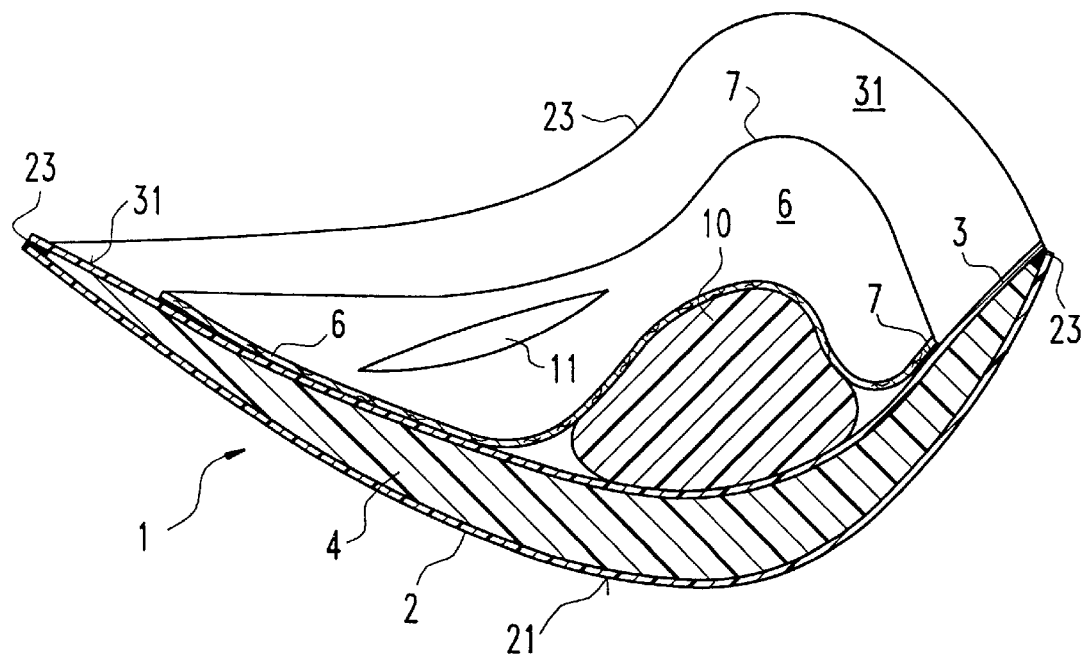
FIG. 2 a cross-sectional view of the breast prosthesis of FIG. 1, wherein filler material is inserted between the thin part and the back side of the plastic body.

For optimally tailoring the cup prosthesis to the remaining or reconstructed breast, respectively, filler material can be introduced between the fabric member 6 and the back side 31 of the plastic body 1 covered by the fabric member 6. FIG. 2 shows the breast prosthesis of FIG. 1 with filler material 10 inserted between the fabric member 6 and the plastic body 1.

The fabric member 6 is preferably provided with a slotted opening 11 for introducing the filler material between the fabric member and the back side 31 of the plastic body and for removing the filler material therefrom. Preferably, on the side of the fabric member 6 facing the plastic body, there is disposed an annular fabric tape in such a way that the edges of the fabric member 6 and of the fabric tape delimiting the opening 11 are precisely superposed.

Preferably, between the fabric member and the fabric tape, there is disposed a plastic sheet which has the same contour as the fabric tape and is superposed congruently with the fabric tape. The plastic sheet is welded over its entire area to both the fabric tape and the fabric member 6. By employing the fabric tape and the plastic sheet, the edges of the opening 11 can be reinforced without the use of a seam.

Figure 3:
FIGS. 3 to 5 a method for making a breast prosthesis of the invention, wherein the breast prosthesis is shown in cross-sectional view during for various fabrication steps.
Figure 4:
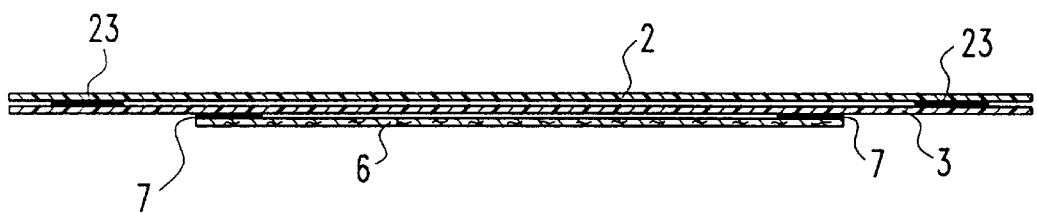
Figure 5:
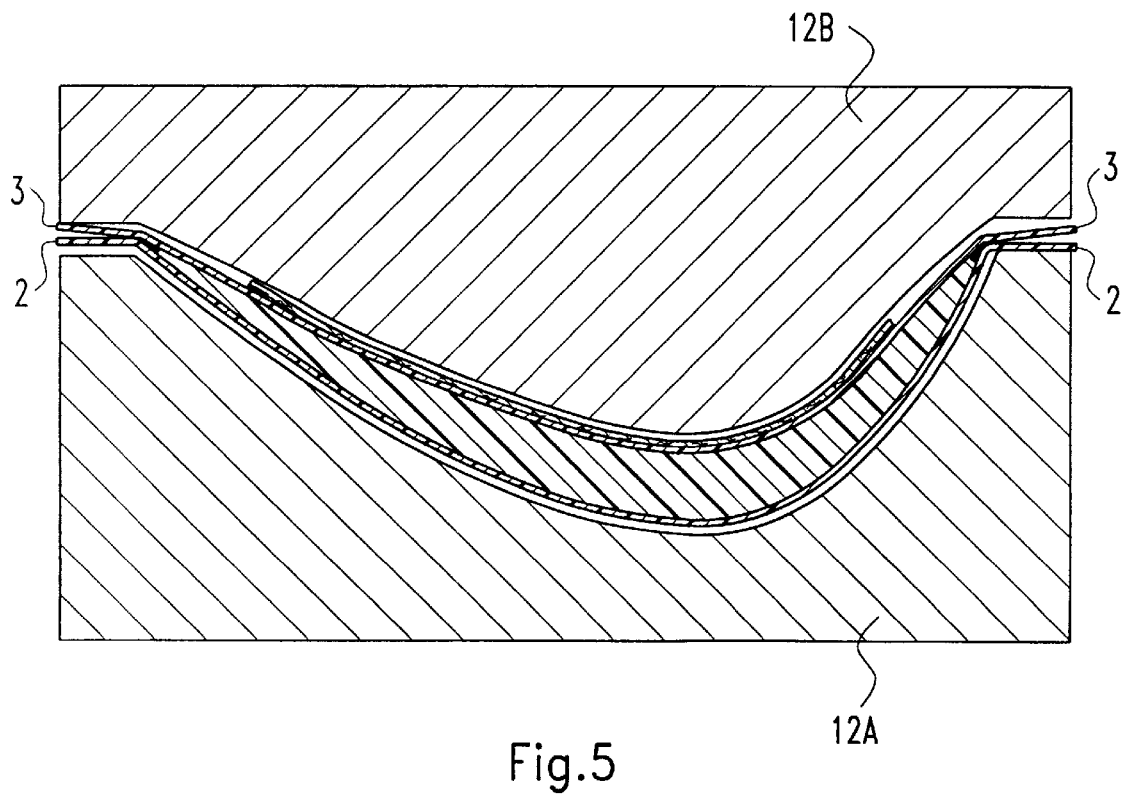

In the following, the preferred method for making a breast prosthesis is described with reference to FIGS. 3 to 5:

(A) First, the fabric member 6 is cut to size and, if necessary, provided with an opening 11. The edge of the opening is preferably reinforced, for example by welding to a plastic sheet and a fabric tape.

(B) In the next step, the so prepared fabric member 6 is secured to a plastic sheet 3 preferably through welding. This state is shown in FIG. 3. The reinforcing fabric tape is preferably disposed between the plastic sheet 3 and the fabric member 6.

(C) Subsequently, another plastic sheet 2 is placed on the side of the plastic sheet 3 facing the fabric member 6 and joined with each other, preferably by welding, along a line 23 which later forms the edge of the prosthesis, except for a fill opening which will be closed later, in such a way that a pouch is formed. The line 23 which later forms the edge of the prosthesis, encloses the edge 7 of the fabric member 6. This state of the method is shown in FIG. 4.

(D) The pouch formed in this manner is then filled with a non-crosslinked silicone rubber mass and placed in a two-part mold form 12A, 12B with a recess, wherein the recess is shaped to correspond to the front of the prosthesis which is shaped to resemble the natural breast. The mold form 12A, 12B is closed in the conventional fashion. During this process, the two plastic sheets 2, 3 and the fabric member 6 are deep drawn. The fabric member 6 preferably comprises synthetic material such that the fabric member 6 is molded during the deep-drawing process and preferably assumes a preformed shape corresponding to the deep drawn back side 31. Alternately, the material can retain its original shape after the deep drawing process, whereby the breast prosthesis is stiffened by the resulting slightly stressed area. The deep-drawn breast prosthesis inside the mold form is shown in FIG. 5. For the sake of clarity, the reference numerals corresponding to those in FIGS. 1 and 2 are omitted in FIG. 5.

(E) Subsequently, the silicone rubber mass is cross-linked inside a hot box. Afterwards, the prosthesis is removed from the mold form 12A, 12B for finish processing, wherein in particular the marginal region of the plastic sheets are cut off up to the connection line 23 which then forms the edge of the completed prosthesis.

Figure 6:
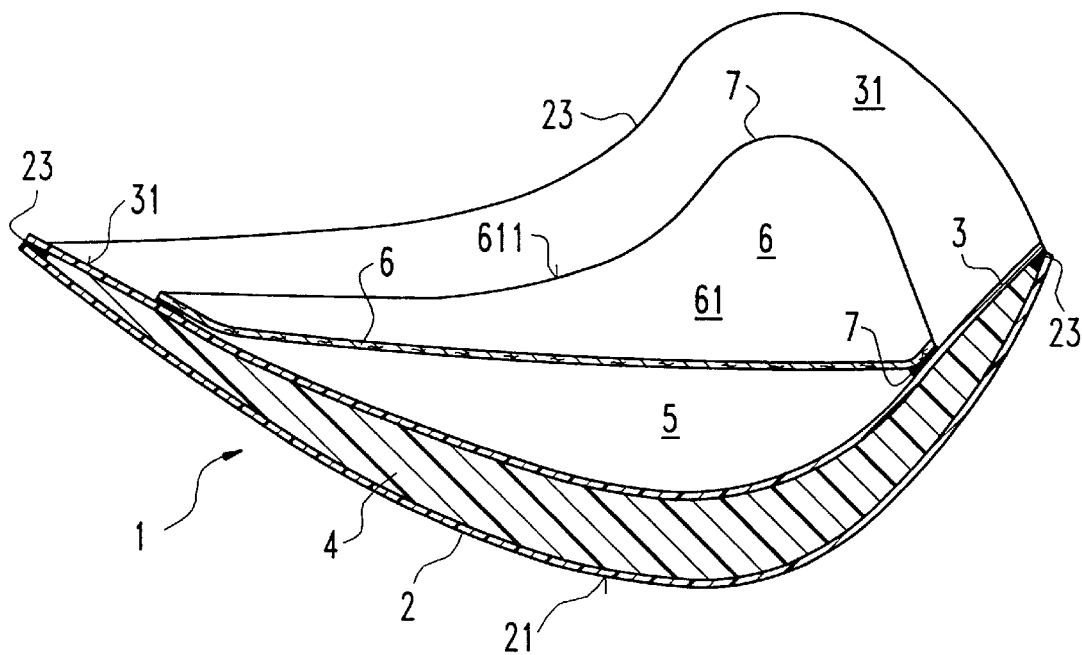
FIG. 6 a cross-sectional view of the breast prosthesis of the invention according to another embodiment.

The breast prosthesis depicted in FIG. 6 comprises a flexible, cup-shaped plastic body 1 including two polyurethane films 2, 3 which are welded together along their common edge 23, and a two component cross-linked silicone rubber mass 4 which is enclosed cavitation-free between the polyurethane films. The side 21 of the polyurethane film 2 facing away from the silicone mass 4 has a convex shape corresponding to the shape of the natural breast. The side 21 of the polyurethane film 2 represents the front side of the plastic body 1 and thus the front side of the breast prosthesis. The side 31 of the polyurethane film 3 facing away from the silicone mass 4 has a concave shape, wherein the concave shape approximately matches the contour of the front side of the plastic body. This side 31 of the polyurethane film 3 represents the back side of the plastic body 1 facing the body of the wearer of the prosthesis. To the back side of the plastic body 1, there is fixedly connected an elastically deformeable fabric member (thin part) 6 through a weld or glue seam 7. The weld or glue seam 7 extends inside the common edge 23 of the two plastic sheets 2, 3. Consequently, the fabric member 6 forms a surface 61 which is closer to the front of the prosthesis than in a breast prosthesis wherein the fabric member is secured only to the common edge 23 of the two plastic sheets 2, 3. The surface area of the surface 61 increases when pressure is applied and the shape of the breast prosthesis changes as a result. The force required in this case generates a force which opposes the deformation. Since the surface 61 is located closer to the front of the prosthesis than is the case with conventional prosthesis, i.e. the surface 61 is located more towards the middle of the prosthesis, the prosthesis can have the same stiffness even if the plastic body 1 is less rigid. The weight of the prosthesis can therefore be reduced and the prosthesis can be worn more comfortably.

Suitably, the edge 611 of the fabric member 6 is disposed in the forward third of the plastic body 1.

A cavity 5 is disposed between the surface 61 and the back side of the plastic body 1 inside the surface 61. If the fabric member 6 is made of microfibers or climate fabrics, respectively, sweat in vapor form which permeated through the fabric member, can condense in the cavity 5. The side facing the wearer remains comfortably dry. Since the volume of the cavity 5 is rather large, the wearer stays dry even after the prosthesis has been worn for a long time.

Instead of a fixed connection between the fabric member 6 and the back side of the plastic body 1, a releasable connection can also be contemplated. A releasable connection is appropriate if the fabric member 6 and the plastic body 1 are to be cleaned separately from each other. A removable fabric member 6 is also advantageous if the cavity 5 contains a padding member, as depicted in the embodiments of FIGS. 9A, 9B, 9C, 10A and 10B and described below, which, if necessary, can be removed, cleaned, exchanged or changed in volume. The fabric member 6 can also be provided with an opening for gaining access to the cavity 5 in order to reach the padding member for the above described purposes or in order to be able to insert the padding member into the cavity at all, wherein an opening may be provided in particular if the fabric member is fixedly secured to the back side of the plastic body. Instead of placing the opening in the fabric member, the opening can also be formed by segmenting the joint seam between the fabric member and the plastic body. A releasable connection between the fabric member and the plastic body can be implemented, for example, through a Velcro closure.

For the sake of brevity, parts having identical reference numbers and the same functionality, will not be described further or will not be referenced at all in the following description of additional embodiments.

Figure 7:
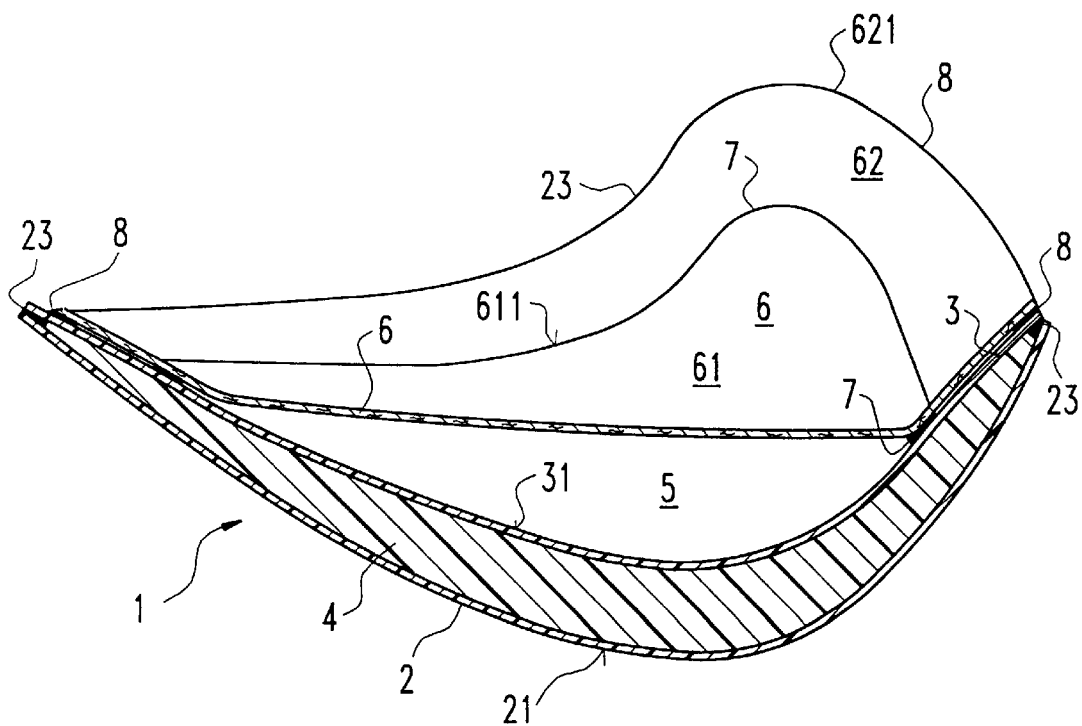
FIG. 7 a cross-sectional view of another embodiment of a breast prosthesis of the invention, wherein the thin part comprises a marginal region.

In the further embodiment of the breast prosthesis depicted in FIG. 7, the fabric member 6 includes, in addition to the central area 61, a marginal region 62 which is fixedly secured to the back side 31 through two weld seams 7 and 8. This marginal region 62 covers also the area providing contact between the breast prosthesis and the skin of the wearer. In addition to the weld seams 7 and 8, the marginal region 62 is fixedly secured to the back side 31 by a grid pattern. The marginal region 62 preferably includes a material which does not irritate the skin, most preferably a microfiber material which allows sweat in the vapor phase to penetrate, but prevents penetration in the liquid phase. Consequently, the contact region between the breast prosthesis and the skin of the wearer of the prosthesis remains dry, thereby ensuring a pleasant wear comfort. In addition, air chambers are created by the grid-like attachment, further improving the wear comfort. The ribbing created by the grid increases the surface area of the side of the prosthesis facing the wearer. When microfiber material is used for covering the marginal region 62, penetrating sweat vapor condenses at the plastic sheet 3. The ribbing provides a secure and slip-free fit of the material.

Figure 8:
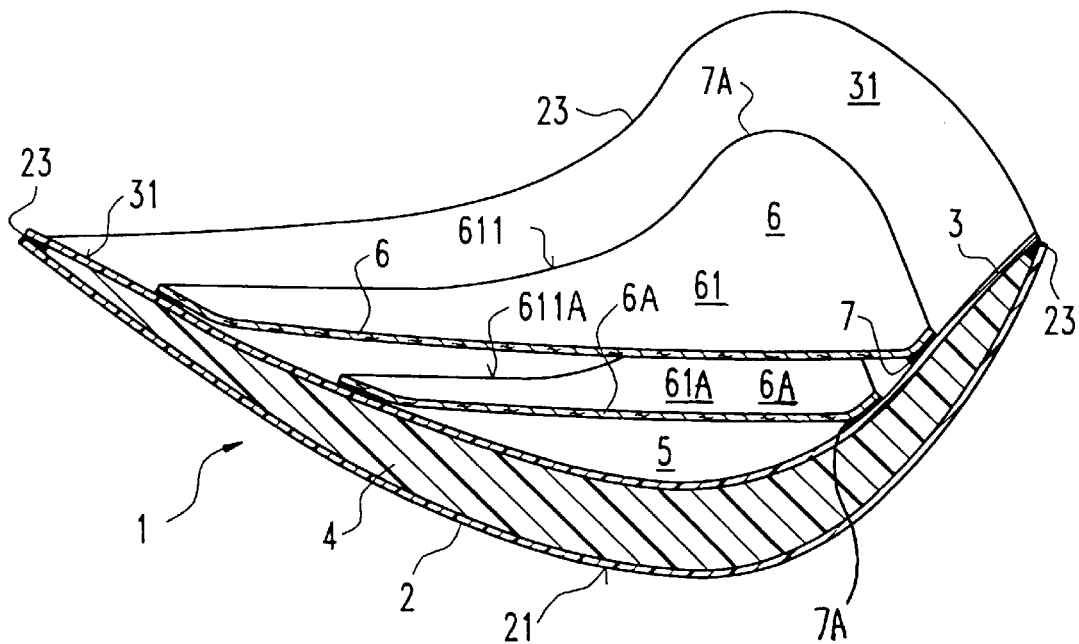
FIG. 8 a cross-sectional view of another embodiment of a breast prosthesis of the invention, wherein there are provided several thin parts.

In FIG. 8 there is shown another embodiment of the breast prosthesis of the invention. This embodiment is similar to the embodiment shown in FIG. 6. In comparison to the embodiment shown in FIG. 6, there is provided an additional thin part 6A having an area 61A. By distributing the areas across a wide region of the height of the prosthesis, the stiffness of the plastic body can be further reduced by employing, for example, a thinner construction, while retaining the stiffness of the breast prosthesis. The simultaneous reduction in weight improves the wear comfort.

Suitably, the edge 611A of the additional thin part 6A is disposed in the forward third of the plastic body 1 and that the edge 611 of the fabric member 6 is disposed in the rearward third of the plastic body 1.

In an alternate embodiment (not shown), the thin part 6 can also be omitted so that only the front region of the breast prosthesis is reinforced by the fabric member 6A. A breast prosthesis of this type is particularly suited for women who underwent a partial amputation where a large part of the breast was not removed. Depending on the support requirements, additional thin parts 6A with areas 61A can be fixedly or releasably secured to the plastic body 1.

Figure 9A:
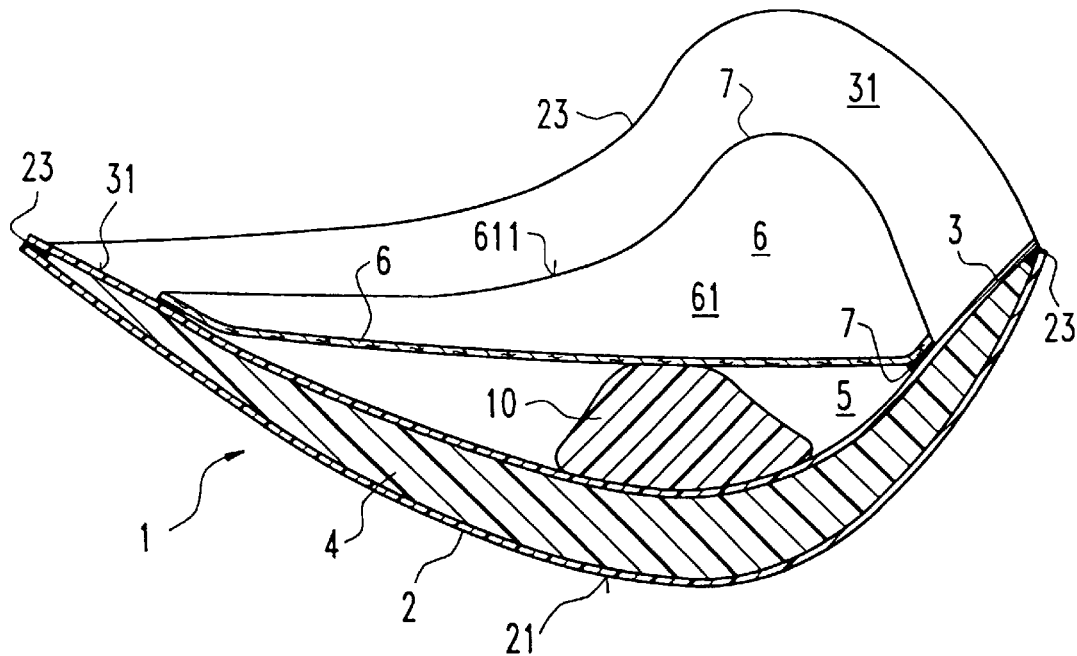
FIGS. 9A, 9B and 9C cross-sectional views of further embodiments of a breast prosthesis of the invention, wherein there is provided a padding element in a cavity between the plastic body and the thin part.
Figure 9B:
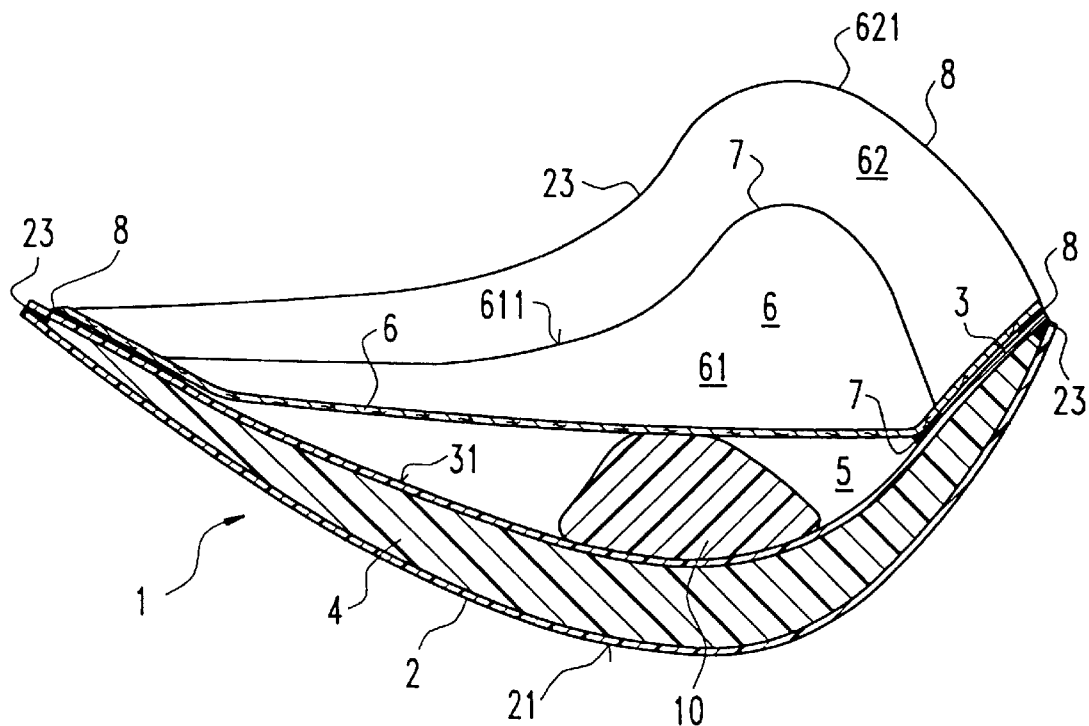
Figure 9C:
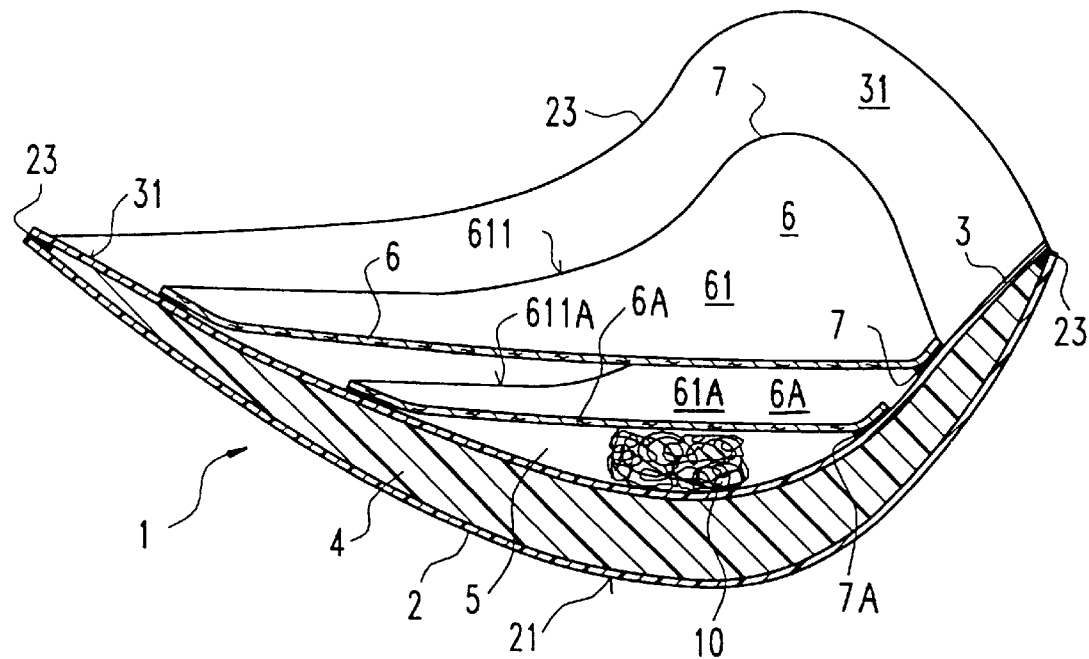

In FIGS. 9A, 9B and 9C, there are shown additional embodiments of the breast prosthesis of the invention corresponding to the embodiments of FIGS. 6, 7 and 8. Only differences with the aforedescribed embodiments will be described hereinafter. For the description of parts already discussed, reference is made to the description of the above figures. In the embodiments of FIGS. 9A, 9B and 9C, a padding member 10 is disposed inside the cavity 5. This padding member 10 can, for example, be a polyurethane film filled with air or a microfiber thread ball or a foam body. The padding member stabilizes the breast prosthesis further without adding significant weight. As a result, the silicone portion or the space between the plastic sheets 2 and 3 could be reduced further, making it possible to manufacture a lighter prosthesis at less cost. Thereby, the wear comfort is further enhanced.

Figure 10A:
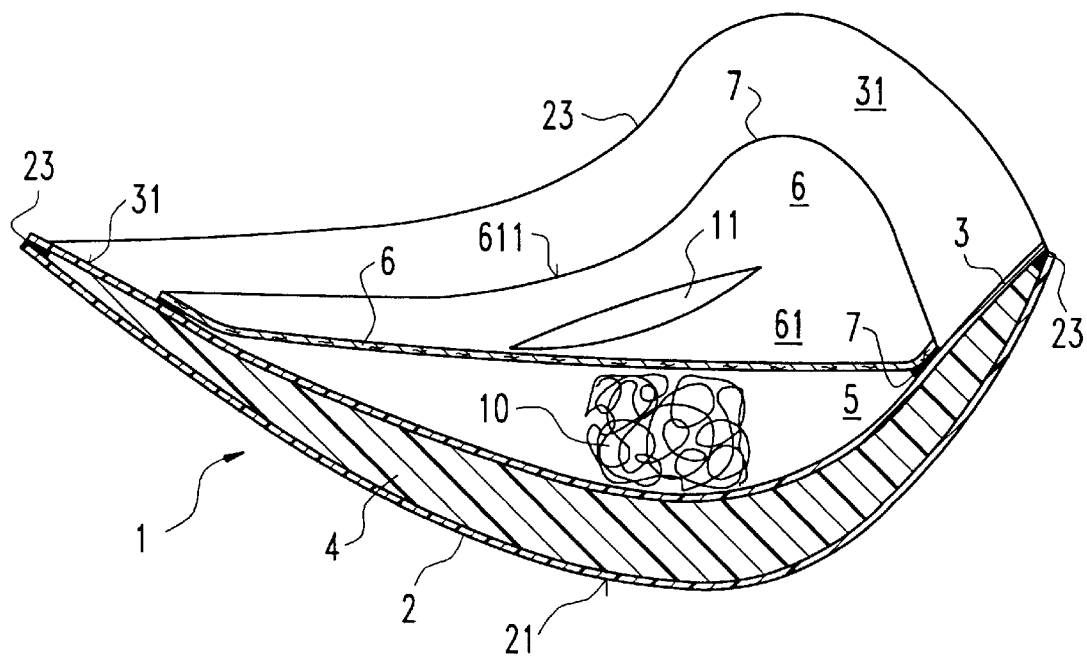
FIGS. 10A, 10B and 10C cross-sectional views of further embodiments of a breast prosthesis of the invention, wherein there is provided an opening for removing or augmenting the padding element.
Figure 10B:
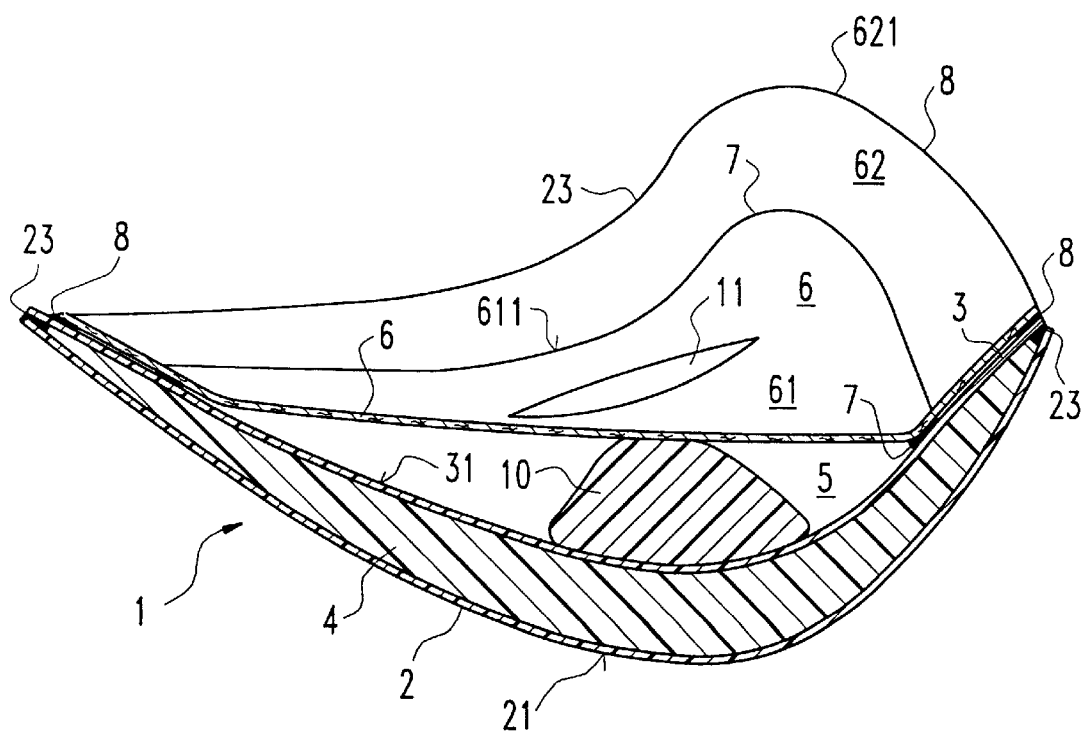

In FIGS. 10A and 10B, there are shown additional embodiments of the prosthesis of the invention corresponding to the embodiment of FIG. 6 and FIG. 7, respectively. Only differences with the aforedescribed embodiments will be described. For the description of parts already discussed, reference is made to the description of the above figures. The embodiment of FIG. 10A comprises as a padding member a microfiber thread ball 10. The thread ball 10 can be removed or enlarged through an opening 11 formed in the area 61. In this way, the stiffness and tension, respectively, can be matched to the human breast to be simulated. The embodiment of FIG. 10B comprises as a padding member a polyurethane ball. Additional padding material can be added or the padding material can be removed through the opening 11. This design provides the above advantages. With both designs, the padding members can be made of other padding materials. These include foam or fiber fill. A padding member filled with air or with another gas or with a fluid can also be employed. Such padding member can be provided with a valve allowing to change the volume and/or the stiffness of the padding member.

Figure 10C:
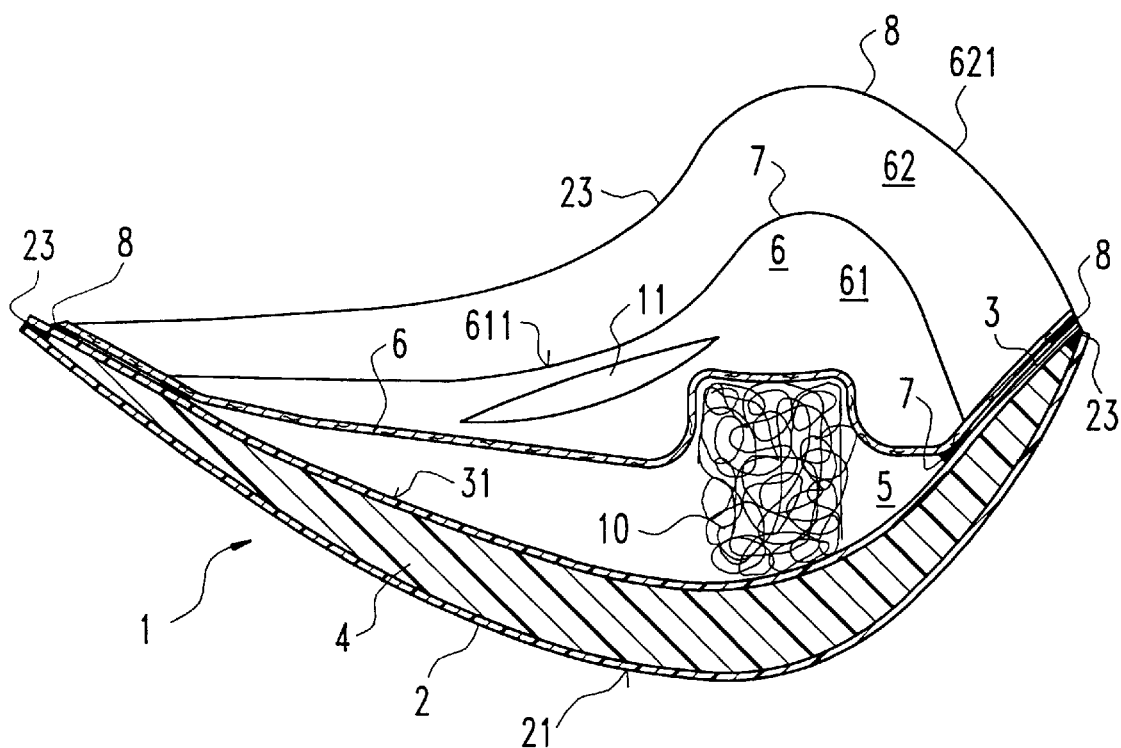

Using a padding member having a changeable shape and volume has the additional advantage that the area formed by the fabric member can be individually matched to the tissue remaining after a partial amputation. An example wherein the area of the fabric member is individually matched by appropriately shaping the padding member, is shown in FIG. 10C.

Figure 11:
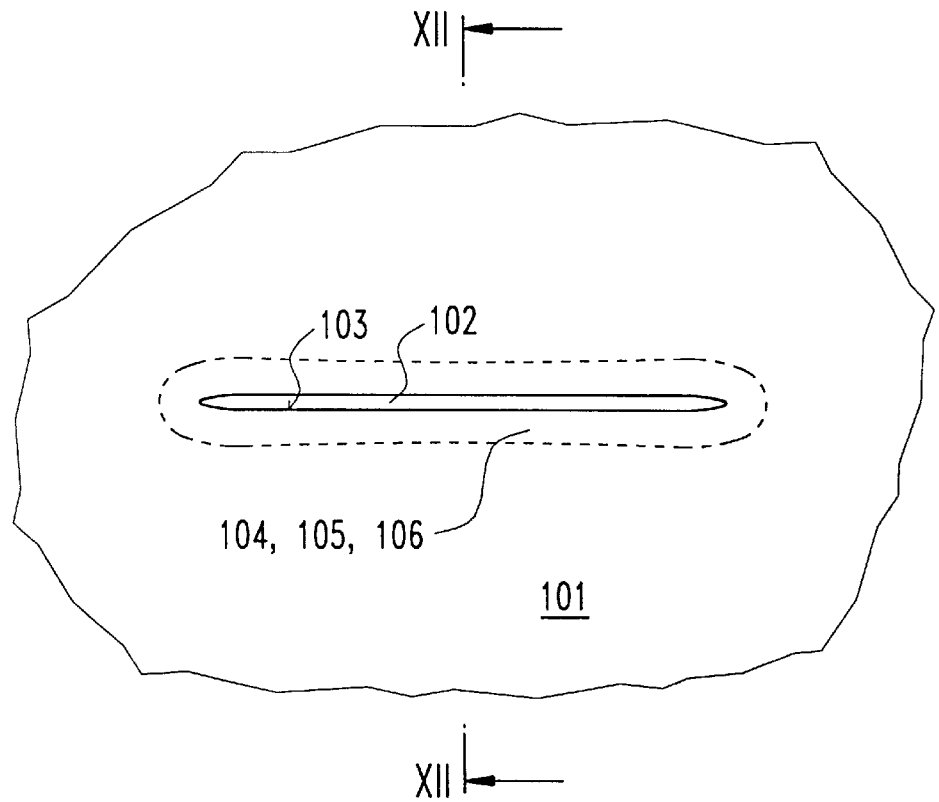
FIG. 11 a top plan view of a partial section of a fabric member with a slotted opening having a reinforced edge according to the invention.
Figure 12:
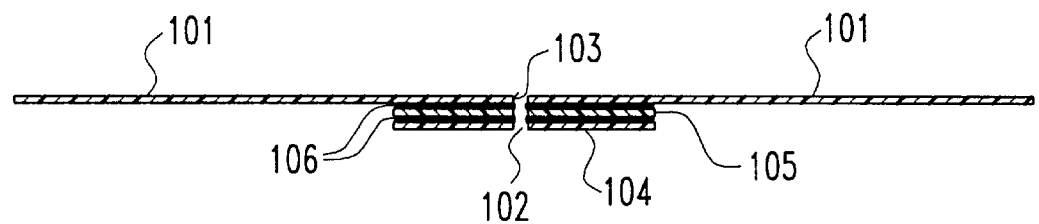
FIG. 12 a cross-sectional view of the fabric member depicted in FIG. 11 taken along the line XII—XII, wherein in addition to the fabric member, there is also shown the fabric tape and the plastic sheet.

In FIGS. 11 and 12, there is shown an advantageous embodiment of the edge of opening 102 which is referenced as 11 in the other figures, wherein the edge is reinforced by placing a plastic sheet 105 between the fabric member 101 (referenced above as 6) and a fabric tape 104 disposed along the edge 103 of the fabric, and by welding or gluing the plastic sheet 105 to the fabric member 101 and the fabric tape 104. The plastic sheet is preferably a polyurethane film and the fabric member 101 and the fabric tape 104 are preferably made of the same material. It should be noted that the thickness of the three elements is exaggerated and that after welding, the plastic sheet in particular will realistically be no longer noticeable in cross section in comparison to the fabric member and the fabric tape.

The fabric member 101 is provided with a slotted opening 102, with the edge 103 of the opening 102 reinforced by placing on the back side of the fabric member 101 an annular fabric tape 104 in such a way that the edges of the fabric member 101 delimiting the opening 102 and of the fabric tape 104 are precisely superposed.

As seen from FIG. 12, between the fabric member 101 and the fabric tape 104, there is placed in congruent superposition with the fabric tape 104 a plastic sheet 105 having the same contour as the fabric tape 104. The plastic sheet 105 is welded over its entire area to both the fabric member 101 and the fabric tape 104. In FIG. 12 as well as in the other Figures, the weld joints are indicated by heavy lines 106.

In FIG. 11, the region of the fabric tape 104, the plastic sheet 105 and the weld joints are indicated by the broken line.

As depicted in FIG. 12, the weld joint can be constructed in such a way that the three members only melt close to their respective surfaces. It is also possible to design the weld joint so that all three members completely fuse together.

What is claimed is:
1. A breast prosthesis, comprising:
   a flexible plastic body including a first plastic sheet member and a second plastic sheet member joined to each other along a common edge,
   a plastic mass enclosed between the first and second plastic sheet members to form a concave cavity, wherein the plastic body has a front face formed to resemble the shape of a natural breast and a back face for facing towards the torso of a wearer; and
   a first elastically deformable thin part secured to the back face of the plastic body which faces towards the torso of the wearer, at a distance, in a range of from 1 to 4 cm from the common edge of the joined first and second plastic sheet members.
2. The breast prosthesis according to claim 1 wherein the edge of the thin part is secured to the back face of the plastic body by at least one weld seam.
3. The breast prosthesis according to claim 1 wherein the edge of the thin part is secured to the back face by a glued seam.
4. The breast prosthesis according to claim 1 wherein the thin part is secured to the back face of the plastic body only along the edge of the thin part.
5. The breast prosthesis according to claim 1, wherein the thin part defines a surface area which in an unstressed state is greater than an area demarcated by the edge of the thin part secured to the plastic body.
6. The breast prosthesis according to claim 1 wherein the thin part defines a surface area which in an unstressed state essentially corresponds to an area of the back face of the plastic body demarcated by the edge of the thin part secured to the plastic body.
7. The breast prosthesis according to claim 1 wherein the thin part is a fabric member.
8. The breast prosthesis according to claim 1 wherein the thin part and the back face of the plastic body define a hollow space, said thin part being provided with an opening for inserting filler material in the hollow space between the thin part and the back (side) face of the plastic body.
9. The breast prosthesis according to claim 8 wherein the opening has the shape of a slit which is demarcated by an edge of the thin part, said edge of the thin part around the opening being reinforced by a fabric tape.
10. The breast prosthesis according to claim 9, and further comprising a plastic sheet disposed between the thin part and the fabric tape and joined to the thin part and the fabric tape by a process selected from the group consisting of welding and gluing.
11. The breast prosthesis according to claim 9 wherein the thin part and the fabric tape are made of a same material.
12. The breast prosthesis according to claim 1 wherein the plastic sheet members are polyurethane films.
13. The breast prosthesis according to claim 1 wherein the thin part in conjunction with the back face of the plastic body forms a cavity.
14. The breast prosthesis according to claim 1 wherein the thin part comprises a marginal region surrounding a central area and extending to the common edge of the first and second plastic sheet members.
15. The breast prosthesis according to claim 14 wherein the marginal region comprises an edge terminating at the common edge of the plastic sheet members, said edge of the marginal region being fixedly secured to the common edge of the plastic sheet members.
16. The breast prosthesis according to claim 15 wherein the edge of the marginal region is welded to the plastic body through a weld seam.

17. The breast prosthesis according to claim 15 wherein the edge of the marginal region is glued to the plastic body.

18. The breast prosthesis according to claim 14 wherein the edge of the marginal region is fixedly secured to the back face of the plastic body in the form of a grid pattern.

19. The breast prosthesis according to claim 1, and further comprising at least one second thin part having an edge which is so affixed to the back face of the plastic body that the first thin part and the second thin part are spaced from one another.

20. The breast prosthesis according to claim 8 wherein the edge of the first thin part is secured to the back face of the plastic body by a weld seam or glue seam, said opening being formed by an interruption in the weld seam or glue seam.

21. The breast prosthesis according to claim 8 wherein the opening is closable.

22. The breast prosthesis according to claim 13, and further comprising a padding member disposed in the cavity.

23. The breast prosthesis according to claim 19 wherein at least one of the first and second thin parts is a fabric member.

24. The breast prosthesis according to claim 23 wherein the fabric member comprises at least one material selected from the group consisting of polyamide fibers, polyester fibers and cotton.

25. The breast prosthesis according to claim 23 wherein the fabric member is made of a material selected from the group consisting of woven fabric and knitted fabric made of microfibers.

26. The breast prosthesis according to claim 25 wherein the microfibers are made of a material selected from the group consisting of polyester and polyamide.

27. The breast prosthesis according to claim 19 wherein at least one of the first and second thin parts is a plastic sheet.

28. The breast prosthesis according to claim 27 wherein the first thin part is a plastic sheet and the second thin part is a fabric member.

29. The breast prosthesis according to claim 2 wherein the edge of the thin part is partially secured to the back face of the plastic body by the weld seam.

30. A breast prosthesis, comprising:
- a flexible plastic body including a first plastic sheet member and a second plastic sheet member joined to each other along a common edge;
- a plastic mass enclosed between the first and second plastic sheet members to form a concave cavity, wherein the plastic body has a front face formed to resemble the shape of a natural breast and a back face for facing towards the torso of a wearer; and
- an elastically deformable thin part secured to the back face of the plastic body at a distance to the common edge of the joined first and second plastic sheet members; wherein the thin part and the back face of the plastic body define a hollow space, said thin part being provided with an opening for inserting filler material in the hollow space between the thin part and the back face of the plastic body, wherein the opening has the shape of a slit which is demarcated by an edge of the thin part, said edge of the thin part around the opening being reinforced by a fabric tape at the edge of the opening.

31. A breast prosthesis, comprising:
- a flexible plastic body including a first plastic sheet member and a second plastic sheet member joined to each other along a common edge;
- a plastic mass enclosed between the first and second plastic sheet members to form a concave cavity, wherein the plastic body has a front face formed to resemble the shape of a natural breast and a back face for facing towards the torso of a wearer; and
- an elastically deformable thin part secured to the back face of the plastic body at a distance to the common edge of the joined first and second plastic sheet members, wherein the thin part and the back face of the plastic body define a hollow space, said thin part being provided with an opening for inserting filler material in the hollow space between the thin part and the back face of the plastic body; wherein the opening has the shape of a slit which is demarcated by an edge of the thin part, said edge of the thin part around the opening being reinforced by a fabric tape at the edge of the opening; and further comprising a plastic sheet disposed between the thin part and the fabric tape and joined to the thin part and the fabric tape by a process selected from the group consisting of welding and gluing.

32. A breast prosthesis, comprising:
- a flexible plastic body including a first plastic sheet member and a second plastic sheet member joined to each other along a common edge;
- a plastic mass enclosed between the first and second plastic sheet members to form a concave cavity, wherein the plastic body has a front face formed to resemble the shape of a natural breast and a back face for facing towards the torso of a wearer; and
- a elastically deformable thin part secured to the back face of the plastic body at a distance to the common edge of the joined first and second plastic sheet members, wherein the thin part and the back face of the plastic body define a hollow space, said thin part being provided with an opening for inserting filler material in the hollow space between the thin part and the back face of the plastic body; wherein the opening has the shape of a slit which is demarcated by an edge of the thin part, said edge of the thin part around the opening being reinforced by a fabric tape at the edge of the opening, wherein the thin part and the fabric tape are made from the same material.

* * * * *